(12) United States Patent
Munchhof et al.

(10) Patent No.: US 7,638,537 B2
(45) Date of Patent: Dec. 29, 2009

(54) PYRAZOLE COMPOUNDS AS TRANSFORMING GROWTH FACTOR (TGF) INHIBITORS

(75) Inventors: Michael J. Munchhof, Salem, CT (US); Laura C. Blumberg, Waterford, CT (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 0 days.

(21) Appl. No.: 11/557,638

(22) Filed: Nov. 8, 2006

(65) Prior Publication Data

US 2007/0117850 A1    May 24, 2007

Related U.S. Application Data

(62) Division of application No. 11/234,564, filed on Sep. 23, 2005, now Pat. No. 7,151,110, which is a division of application No. 10/667,189, filed on Sep. 17, 2003, now Pat. No. 6,958,354.

(60) Provisional application No. 60/484,543, filed on Jul. 2, 2003, provisional application No. 60/412,146, filed on Sep. 18, 2002.

(51) Int. Cl.
*A61K 31/4439* (2006.01)
*C07D 401/14* (2006.01)

(52) U.S. Cl. ...................... 514/333; 546/256
(58) Field of Classification Search ................. 546/256; 514/333
See application file for complete search history.

(56) References Cited

U.S. PATENT DOCUMENTS

| 4,925,857 | A | * | 5/1990 | Bailey et al. ................ 514/341 |
| 6,958,354 | B2 | | 10/2005 | Munchhof et al. |
| 7,030,125 | B2 | | 4/2006 | Munchhof et al. |
| 7,053,095 | B2 | | 5/2006 | Munchhof et al. |
| 2004/0106608 | A1 | | 6/2004 | Munchhof et al. |
| 2004/0110797 | A1 | | 6/2004 | Munchhof et al. |
| 2004/0176390 | A1 | | 9/2004 | Blumberg et al. |
| 2006/0025451 | A1 | | 2/2006 | Munchhof et al. |

FOREIGN PATENT DOCUMENTS

| EP | 0388691 | 9/1990 |
| EP | 1382603 | 1/2004 |
| WO | WO 98/52937 | 11/1998 |
| WO | WO 98/52941 | 11/1998 |
| WO | WO 00/31063 | 6/2000 |
| WO | WO 00/61576 | 10/2000 |
| WO | WO 01/62756 | 8/2001 |
| WO | WO 01/72737 | 10/2001 |
| WO | WO 02/16359 | 2/2002 |
| WO | WO 02/40468 | 5/2002 |
| WO | WO 02/40476 | 5/2002 |
| WO | WO 02/055077 | 7/2002 |
| WO | WO 02/62787 | 8/2002 |
| WO | WO 02/62794 | 8/2002 |
| WO | WO 02/66462 | 8/2002 |
| WO | WO 02/088107 | 11/2002 |
| WO | WO 03/087304 | 10/2003 |
| WO | WO 2004/013135 | 2/2004 |

OTHER PUBLICATIONS

Vippagunta et al., "Crystalline Solid", Advanced Drug Delivery Reviews 48 (2001) 3-26.*
Guillory (in Brtittain ed)., "Polymorphism, etc.," NY: Marcel Dekker, Inc., 1999, 1-2, 183-226.*
Singh et al., "Successful Shape-Based Virtual Screening: The Discovery of a Potent Inhibitor of the Type I TGFbeta Receptor Kinase (TbetaRI)", Bioorganic & Medicinal Chemistry Letters, vol. 13, No. 24, 2003, pp. 4355-4359.
Database Caplus 'Online! Beilstein Institut zur Foerderung der Chemischen Wissenschaften, Frankfurt am Main, DE; Database accession No. 1220267, XP-002262347, 2,2'-(4-phenyl-1H-pyrazole-3,5-diyl)-bis-pyridine, abstract.
Database Caplus 'Online! Bellstein Institut zur Foerderung der Chemischen Wissenschaften, Frankfurt am Main, DE; Database accession No. 1181440, XP-002262348, 2,2'-[1-(3-methyl-2-phenyl-aziridin-2-yl)-4-phenyl-1H-pyrazole-3,5-diyl]-bis-pyridine, abstract.
Database Caplus 'Online! Chemical Abstracts Service, accession No. 1993:472619, Database accession No. 119:72619, XP-002262349, Preparation of pyrazole and 4H-pyrazolo[1,5-a]pyrimidin-5-one derivatives as antiinflammatory, antirheumatic, antibacterial, and antiviral agents, abstract.
Database Caplus 'Online! Chemical Abstracts Service, accession No. 2000:881141, Database accession No. 134:29414, XP-002262350, Preparation of substituted pyrazole compounds as p38 MAP kinase inhibitors, abstract.
Database Caplus 'Online! Chemical Abstracts Service, accession No. 1996:607249, Database accession No. 125:247806, XP-002262351, Preparation of pyrazole derivatives as antiviral agents, abstract.
PCT International Search Report from PCT/IB03/03933, mailed Mar. 2, 2004.
Sloan et al., "Comparison of the effects of single doses of morphine and thebaine on body temperature, activity, and brain and heart levels of catechol amines and serotonin", cited in Chem Abstracts, AN 1964:19085, 2002.

* cited by examiner

*Primary Examiner*—Patricia L Morris
(74) *Attorney, Agent, or Firm*—John H. Engelmann; Lucy X. Yang

(57) ABSTRACT

Novel pyrazole compounds, including derivatives thereof, to intermediates for their preparation, to pharmaceutical compositions containing them and to their medicinal use are described. The compounds of the present invention are potent inhibitors of transforming growth factor ("TGF")- β signaling pathway. They are useful in the treatment of various TGF-related disease states including, for example, cancer, and fibrotic diseases.

3 Claims, No Drawings

PYRAZOLE COMPOUNDS AS TRANSFORMING GROWTH FACTOR (TGF) INHIBITORS

RELATED APPLICATIONS

This application is a divisional application of U.S. patent application Ser. No. 11/234,564 filed Sep. 23, 2005, now U.S. Pat. No. 7,151,110 issued Dec. 19, 2006, which is a divisional of U.S. patent application Ser. No. 10/667,189 filed Sep. 17, 2003, now U.S. Pat. No. 6,958,354 issued Oct. 25, 2005, which claims the benefit of priority under 35 USC 119(e) to U.S. Provisional Application Nos. 60/412,146 filed Sep. 18, 2002, and 60/484,543 filed Jul. 2, 2003, each of which are herein incorporated in its entirety by reference.

BACKGROUND OF THE INVENTION

The present invention relates to novel pyrazole compounds, including derivatives thereof, to intermediates for their preparation, to pharmaceutical compositions containing them and to their medicinal use. The compounds of the present invention are potent inhibitors of the transforming growth factor ("TGF")-β signaling pathway. They are useful in the treatment of TGF-β related disease states including, for example, cancer and fibrotic diseases.

TGF-β activates both antiproliferative and tumor-promoting signaling cascades. Three mammalian TGF-β isoforms have been identified (TGF-βI, -βII, and -βIII). TGF-β production promotes tumor progression while its blockade enhances antitumor activity. Blockade of TGF-β enhances antitumor immune responses and inhibits metastasis. Thus there exists a need in the art for compounds that inhibit the TGF-β signaling pathway. The present invention, as described below, answers such a need.

SUMMARY OF THE INVENTION

The present invention provides a novel compound containing a core pyrazole ring substituted with at least one substituted or unsubstituted 2-pyridyl moiety and at least one $R^1$ moiety as set forth herein, and all pharmaceutically acceptable salts, prodrugs, tautomers, hydrates and solvates thereof. In a compound of the invention, the substituted or unsubstituted 2-pyridyl moiety and $R^1$ moiety can be in an 1,2-, 1,3- or 1,4-relationship around the core pyrazole ring; preferably, in an 1,2- or ortho relationship.

The present invention provides a compound of formula (Ia):

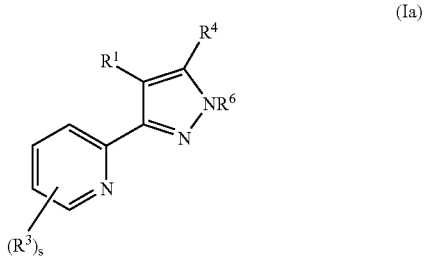

(Ia)

and all pharmaceutically acceptable salts, prodrugs, tautomers, hydrates and solvates thereof, where $R^1$, $R^3$, $R^4$, $R^6$ and s are each as set forth herein, with the proviso that $R^1$ contains at least one heteroatom.

In formula (Ia), as set forth above:
$R^1$ is a saturated, unsaturated, or aromatic $C_3$-$C_{20}$ mono-, bi- or polycyclic ring optionally containing at least one heteroatom selected from the group consisting of N, O and S, wherein $R^1$ can optionally be further independently substituted with at least one moiety independently selected from the group consisting of: carbonyl, halo, halo($C_1$-$C_6$)alkyl, perhalo($C_1$-$C_6$)alkyl, perhalo($C_1$-$C_6$)alkoxy, ($C_1$-$C_6$)alkyl, ($C_2$-$C_6$)alkenyl, ($C_2$-$C_6$)alkynyl, hydroxy, oxo, mercapto, ($C_1$-$C_6$) alkylthio, ($C_1$-$C_6$)alkoxy, ($C_5$-$C_{10}$)aryl or ($C_5$-$C_{10}$) heteroaryl, ($C_5$-$C_{10}$)aryloxy or ($C_5$-$C_{10}$)heteroaryloxy, ($C_5$-$C_{10}$)ar($C_1$-$C_6$)alkyl or ($C_5$-$C_{10}$)heteroar($C_1$-$C_6$)alkyl, ($C_5$-$C_{10}$)ar($C_1$-$C_6$)alkoxy or ($C_5$-$C_{10}$)heteroar($C_1$-$C_6$)alkoxy, HO—(C=O)—, ester, amido, ether, amino, amino($C_1$-$C_6$) alkyl, ($C_1$-$C_6$)alkylamino($C_1$-$C_6$)alkyl, di($C_1$-$C_6$)alkylamino ($C_1$-$C_6$)alkyl, ($C_5$-$C_{10}$)heterocyclyl($C_1$-$C_6$)alkyl, ($C_1$-$C_6$) alkyl- and di($C_1$-$C_6$)alkylamino, cyano, nitro, carbamoyl, ($C_1$-$C_6$)alkylcarbonyl, ($C_1$-$C_6$)alkoxycarbonyl, ($C_1$-$C_6$)alkylaminocarbonyl, di($C_1$-$C_6$)alkylaminocarbonyl, ($C_5$-$C_{10}$) arylcarbonyl, ($C_5$-$C_{10}$)aryloxycarbonyl, ($C_1$-$C_6$)alkylsulfonyl, and ($C_5$-$C_{10}$)arylsulfonyl;

preferably, $R^1$ can optionally be further independently substituted with zero to two moieties independently selected from the group consisting of, but not limited to, halo($C_1$-$C_6$) alkyl, perhalo($C_1$-$C_6$)alkyl, perhalo($C_1$-$C_6$)alkoxy, ($C_1$-$C_6$) alkyl, ($C_1$-$C_6$)alkoxy, ($C_5$-$C_{10}$)ar($C_1$-$C_6$)alkoxy or ($C_5$-$C_{10}$) heteroar($C_1$-$C_6$)alkoxy, amino, amino($C_1$-$C_6$)alkyl, ($C_1$-$C_6$) alkylamino($C_1$-$C_6$)alkyl, di($C_1$-$C_6$)alkylamino($C_1$-$C_6$)alkyl, and ($C_5$-$C_{10}$)heterocyclyl($C_1$-$C_6$)alkyl;

each $R^3$ is independently selected from the group consisting of: hydrogen, halo, halo($C_1$-$C_6$)alkyl, ($C_1$-$C_6$)alkyl, ($C_2$-$C_6$)alkenyl, ($C_2$-$C_6$)alkynyl, perhalo($C_1$-$C_6$)alkyl, phenyl, ($C_5$-$C_{10}$)heteroaryl, ($C_5$-$C_{10}$)heterocyclic, ($C_3$-$C_{10}$)cycloalkyl, hydroxy, ($C_1$-$C_6$)alkoxy, perhalo($C_1$-$C_6$)alkoxy, phenoxy, ($C_5$-$C_{10}$)heteroaryl-O—, ($C_5$-$C_{10}$)heterocyclic-O—, ($C_3$-$C_{10}$)cycloalkyl-O—, ($C_1$-$C_6$)alkyl-S—, ($C_1$-$C_6$) alkyl-SO$_2$—, ($C_1$-$C_6$)alkyl-NH—SO$_2$—, O$_2$N—, NC—, amino, Ph(CH$_2$)$_{1-6}$HN—, ($C_1$-$C_6$)alkyl HN—, ($C_1$-$C_6$)alkylamino, [($C_1$-$C_6$)alkyl]$_2$-amino, ($C_1$-$C_6$)alkyl-SO$_2$—NH—, amino(C=O)—, aminoO$_2$S—, ($C_1$-$C_6$)alkyl-(C=O)—NH—, ($C_1$-$C_6$)alkyl-(C=O)-[(($C_1$-$C_6$)alkyl)-N]-, phenyl-(C=O)—NH—, phenyl-(C=O)-[(($C_1$-$C_6$)alkyl)-N]-, ($C_1$-$C_6$)alkyl-(C=O)—, phenyl-(C=O)—, ($C_5$-$C_{10}$)heteroaryl-(C=O)—, ($C_5$-$C_{10}$)heterocyclic-(C=O)—, ($C_3$-$C_{10}$) cycloalkyl-(C=O)—, HO—(C=O)—, ($C_1$-$C_6$)alkyl-O—(C=O)—, H$_2$N(C=O)—, ($C_1$-$C_6$)alkyl-NH—(C=O)—, [($C_1$-$C_6$)alkyl]$_2$—N—(C=O)—, phenyl-NH—(C=O)—, phenyl-[(($C_1$-$C_6$)alkyl)-N]-(C=O)—, ($C_5$-$C_{10}$)heteroaryl-NH—(C=O)—, ($C_5$-$C_{10}$)heterocyclic-NH—(C=O)—, ($C_3$-$C_{10}$)cycloalkyl-NH—(C=O)— and ($C_1$-$C_6$)alkyl-(C=O)—O—; preferably, $R^3$ is hydrogen or ($C_1$-$C_6$)alkyl; more preferably, $R^3$ is hydrogen or methyl;

where alkyl, alkenyl, alkynyl, phenyl, heteroaryl, heterocyclic, cycloalkyl, alkoxy, phenoxy, amino of $R^3$ is optionally substituted by at least one substituent independently selected from ($C_1$-$C_6$)alkyl, ($C_1$-$C_6$)alkoxy, halo($C_1$-$C_6$)alkyl, halo, H$_2$N—, Ph(CH$_2$)$_{1-6}$HN—, and ($C_1$-$C_6$)alkylHN—;

s is an integer from one to five; preferably, one to two; more preferably, one;

$R^4$ is selected from the group consisting of: hydrogen, halo, halo($C_1$-$C_6$)alkyl, ($C_1$-$C_6$)alkyl, ($C_2$-$C_6$)alkenyl, ($C_2$-$C_6$) alkynyl, perhalo($C_1$-$C_6$)alkyl, phenyl, ($C_5$-$C_{10}$)heteroaryl, ($C_5$-$C_{10}$)heterocyclic, ($C_3$-$C_{10}$)cycloalkyl, hydroxy, ($C_1$-$C_6$) alkoxy, perhalo($C_1$-$C_6$)alkoxy, phenoxy, ($C_5$-$C_{10}$)heteroaryl-O—, ($C_5$-$C_{10}$)heterocyclic-O—, ($C_3$-$C_{10}$)cycloalkyl-O—, ($C_1$-$C_6$)alkyl-S—, ($C_1$-$C_6$)alkyl-SO$_2$—, ($C_1$-$C_6$)alkyl-NH—SO$_2$—, O$_2$N—, NC—, amino, Ph(CH$_2$)$_{1-6}$NH—, alkylNH—, $(C_1-C_6)$alkylamino, $[(C_1-C_6)alkyl]_2$-amino, $(C_1-C_6)$alkyl-$SO_2$—NH—, amino(C=O)—, amino$SO_2$—, $(C_1-C_6)$alkyl-(C=O)—NH—, $(C_1-C_6)$alkyl-(C=O)—(($C_1-C_6$)alkyl)-N]-, phenyl-(C=O)—NH—, phenyl-(C=O)—(($C_1-C_6$)alkyl)-N]-, $(C_1-C_6)$alkyl-(C=O)—, phenyl-(C=O)—, $(C_5-C_{10})$heteroaryl-(C=O)—, $(C_5-C_{10})$heterocyclic-(C=O)—, $(C_3-C_{10})$cycloalkyl-(C=O)—, HO—(C=O)—, $(C_1-C_6)$alkyl-O—(C=O)—, $H_2N$(C=O)—, $(C_1-C_6)$alkyl-NH—(C=O)—, (($C_1-C_6$)alkyl)$_2$-N—(C=O)—, phenyl-NH—(C=O)—, phenyl-(($C_1-C_6$)alkyl)-N]-(C=O)—, $(C_5-C_{10})$heteroaryl-NH—(C=O)—, $(C_5-C_{10})$heterocyclic-NH—(C=O)—, $(C_3-C_{10})$cycloalkyl-NH—(C=O)— and $(C_1-C_6)$alkyl-(C=O)—O—; preferably, $R^4$ is hydrogen, $(C_1-C_6)$alkyl, $(C_3-C_{10})$cycloalkyl, amino, $(C_1-C_6)$alkylamino, $(C_1-C_6)$alkyl-(C=O)—, or $(C_3-C_{10})$cycloalkyl-(C=O)—;

where alkyl, alkenyl, alkynyl, phenyl, heteroaryl, heterocyclic, cycloalkyl, alkoxy, phenoxy, and amino of $R^4$ is optionally substituted by at least one substituent independently selected from the group consisting of $(C_1-C_6)$alkyl, $(C_1-C_6)$alkoxy, halo$(C_1-C_6)$alkyl, halo, $H_2N$—, Ph$(CH_2)_{1-6}$—NH—, and $(C_1-C_6)$alkylNH—; and $R^6$ is selected from the group consisting of hydrogen, $(C_1-C_6)$alkyl, $(C_2-C_6)$alkenyl, $(C_2-C_6)$alkynyl, phenyl, $(C_5-C_{10})$heteroaryl, $(C_5-C_{10})$heterocyclic, $(C_3-C_{10})$cycloalkyl, $(C_1-C_6)$alkyl-(SO$_2$)—, phenyl-(SO$_2$)—, $H_2N$—(SO$_2$)—, $(C_1-C_6)$alkyl-NH—(SO$_2$)—, (($C_1-C_6$)alkyl)$_2$N—(SO$_2$)—, phenyl-NH—(SO$_2$)—, (phenyl)$_2$N—(SO$_2$)—, $(C_1-C_6)$alkyl-(C=O)—, phenyl-(C=O)—, $(C_5-C_{10})$heteroaryl-(C=O)—, $(C_5-C_{10})$heterocyclic-(C=O)—, $(C_3-C_{10})$cycloalkyl-(C=O)—, $(C_1-C_6)$alkyl-O—(C=O)—, $(C_5-C_{10})$heterocyclic-O—(C=O)—, $(C_3-C_{10})$cycloalkyl-O—(C=O)—, $H_2N$—(C=O)—, $(C_1-C_6)$alkyl-NH—(C=O)—, phenyl-NH—(C=O)—, $(C_5-C_{10})$heteroaryl-NH—(C=O)—, $(C_5-C_{10})$heterocyclic-NH—(C=O)—, $(C_3-C_{10})$cycloalkyl-NH—(C=O)—, (($C_1-C_6$)alkyl)$_2$N—(C=O)—, (phenyl)$_2$N—(C=O)—, phenyl-[(($C_1-C_6$)alkyl)-N]-(C=O)—, $(C_5-C_{10})$heteroaryl-[(($C_1-C_6$)alkyl)-N]-(C=O)—, $(C_5-C_{10})$heterocyclic-[(($C_1-C_6$)alkyl)-N]-(C=O)—, and $(C_3-C_{10})$cycloalkyl-[(($C_1-C_6$)alkyl)-N]-(C=O)—; preferably, $R^6$ is hydrogen or $(C_1-C_6)$alkyl; more preferably, hydrogen or methyl;

where alkyl, alkenyl, alkynyl, phenyl, benzyl, heteroaryl, heterocyclic, cycloalkyl, alkoxy, phenoxy, amino of $R^6$ is optionally substituted with at least one moiety independently selected from the group consisting of halo, $(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_5-C_{10})$heterocyclic, $(C_5-C_{10})$heteroaryl, $(C_1-C_6)$alkyl-SO$_2$—, formyl, NC—, $(C_1-C_6)$alkyl-(C=O)—, $(C_3-C_{10})$cycloalkyl-(C=O)—, phenyl-(C=O)—, $(C_5-C_{10})$heterocyclic-(C=O)—, $(C_5-C_{10})$heteroaryl-(C=O)—, HO—(C=O)—, $(C_1-C_6)$alkyl-O—(C=O)—, $(C_3-C_{10})$cycloalkyl-O—(C=O)—, $(C_5-C_{10})$heterocyclic-O—(C=O)—, $(C_1-C_6)$alkyl-NH—(C=O)—, $(C_3-C_{10})$cycloalkyl-NH—(C=O)—, phenyl-NH—(C=O)—, $(C_5-C_{10})$heterocyclic-NH—(C=O)—, $(C_5-C_{10})$heteroaryl-NH—(C=O)—, (($C_1-C_6$)alkyl)$_2$-N—(C=O)—, phenyl-[(($C_1-C_6$)alkyl)-N]-(C=O)—, hydroxy, $(C_1-C_6)$alkoxy, perhalo$(C_1-C_6)$alkoxy, $(C_3-C_{10})$cycloalkyl-O—, phenoxy, $(C_5-C_{10})$heterocyclic-O—, $(C_5-C_{10})$heteroaryl-O—, $(C_1-C_6)$alkyl-(C=O)—O—, $(C_3-C_{10})$cycloalkyl-(C=O)—O—, phenyl-(C=O)—O—, $(C_5-C_{10})$heterocyclic-(C=O)—O—, $(C_5-C_{10})$heteroaryl-(C=O)—O—, $O_2N$—, amino, $(C_1-C_6)$alkylamino, (($C_1-C_6$)alkyl)$_2$-amino, formamidyl, $(C_1-C_6)$alkyl-(C=O)—NH—, $(C_3-C_{10})$cycloalkyl-(C=O)—NH—, phenyl-(C=O)—NH—, $(C_5-C_{10})$heterocyclic-(C=O)—NH—, $(C_5-C_{10})$heteroaryl-(C=O)—NH—, $(C_1-C_6)$alkyl-(C=O)-[(($C_1-C_6$)alkyl)-N]-, phenyl-(C=O)-[(($C_1-C_6$)alkyl-N]-, $(C_1-C_6)$alkyl-SO$_2$NH—, $(C_3-C_{10})$cycloalkyl-SO$_2$NH—, phenyl-SO$_2$NH—, $(C_5-C_{10})$heterocyclic-SO$_2$NH— and $(C_5-C_{10})$heteroaryl-SO$_2$NH—; preferably, $R^6$ is substituted with zero to two groups independently selected from the group consisting of $(C_1-C_6)$alkyl and $(C_3-C_{10})$cycloalkyl;

wherein the phenyl or heteroaryl moiety of a $R^6$ substituent is optionally further substituted with at least one radical independently selected from the group consisting of halo, $(C_1-C_6)$alkyl, $(C_1-C_6)$alkoxy, perfluoro$(C_1-C_6)$alkyl and perfluoro$(C_1-C_6)$alkoxy; with the proviso that $R^1$ contains at least one heteroatom.

In another embodiment of the invention, $R^1$ of formula (Ia), as set forth above, is

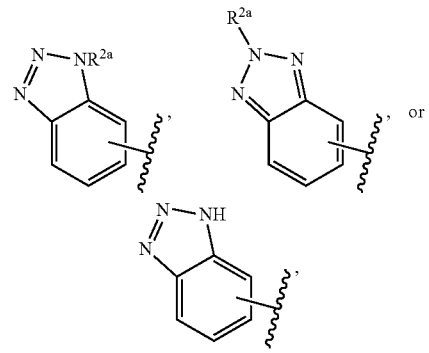

where $R^{2a}$ is as set forth herein.

In another embodiment of the invention, $R^1$ of formula (Ia), as set forth above, is

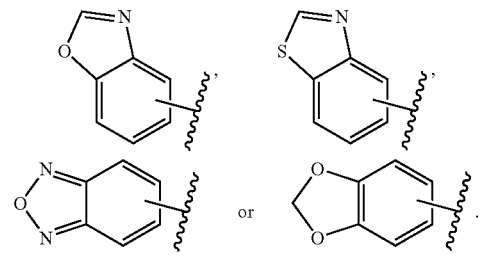

In another embodiment of the invention, $R^1$ of formula (Ia), as set forth above, is

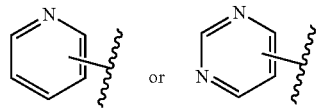

In another embodiment of the invention, $R^1$ of formula (Ia), as set forth above, is

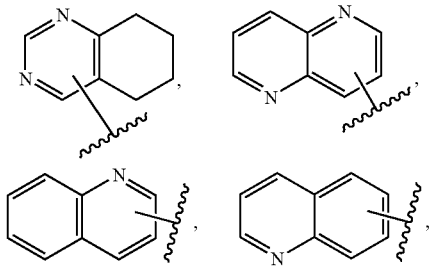

-continued

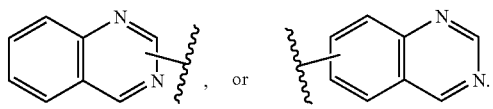

In another embodiment of the invention, $R^1$ of formula (Ia), as set forth above, is

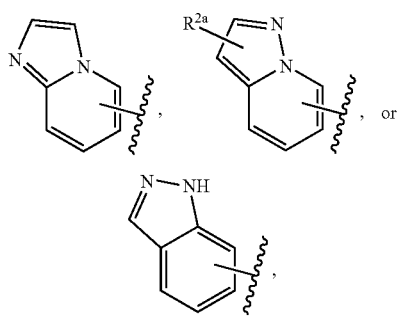

where $R^{2a}$ is as set forth herein.

In another embodiment of the invention, $R^1$ of formula (Ia), as set forth above, is

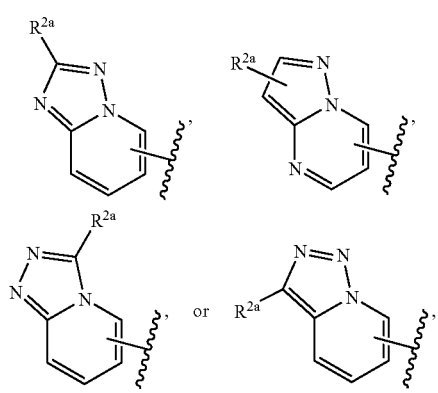

where $R^{2a}$ is as set forth herein.

In another embodiment of the invention, $R^1$ of formula (Ia), as set forth above, is

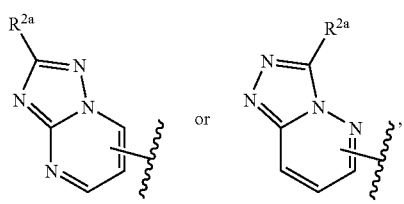

where $R^{2a}$ is as set forth herein.

Each of $R^1$ above can optionally be further substituted by at least one $R^{2a}$ group, as set forth herein.

In another embodiment of the invention, $R^1$ of formula (Ia), as set forth above, is

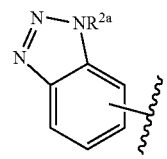

where $R^{2a}$ is as set forth herein.

In another embodiment of the invention, $R^1$ of formula (Ia), as set forth above, is

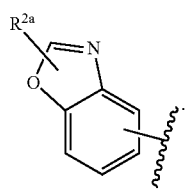

In another embodiment of the invention, $R^1$ of formula (Ia), as set forth above, is

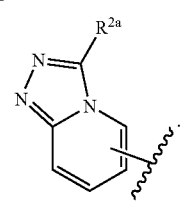

In another embodiment of the invention, $R^1$ of formula (Ia), as set forth above, is

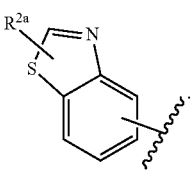

In another embodiment of the invention, $R^1$ of formula (Ia), as set forth above, is

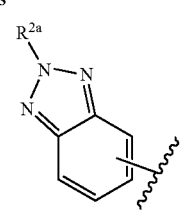

where $R^{2a}$ is as set forth herein.

In another embodiment of the invention, $R^1$ of formula (Ia), as set forth above, is

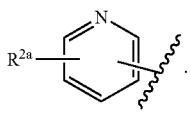

In another embodiment of the invention, R¹ of formula (Ia), as set forth above, is

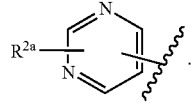

In another embodiment of the invention, R¹ of formula (Ia), as set forth above, is

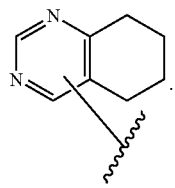

In another embodiment of the invention, R¹ of formula (Ia), as set forth above, is

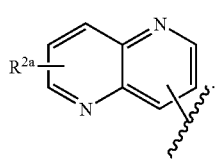

In another embodiment of the invention, R¹ of formula (Ia), as set forth above, is

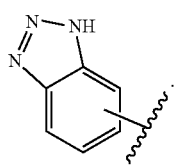

In another embodiment of the invention, R¹ of formula (Ia), as set forth above, is

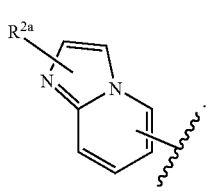

In another embodiment of the invention, R¹ of formula (Ia), as set forth above, is

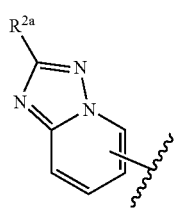

where $R^{2a}$ is as set forth herein.

In another embodiment of the invention, R¹ of formula (Ia), as set forth above, is

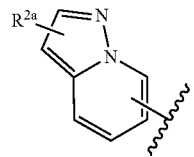

where $R^{2a}$ is as set forth herein.

In another embodiment of the invention, R¹ of formula (Ia), as set forth above, is

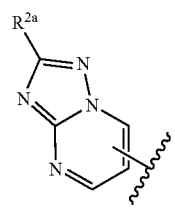

where $R^{2a}$ is as set forth herein.

In another embodiment of the invention, R¹ of formula (Ia), as set forth above, is

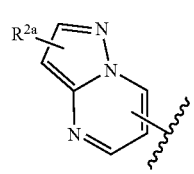

where $R^{2a}$ is as set forth herein.

In another embodiment of the invention, R¹ of formula (Ia), as set forth above, is

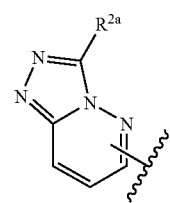

where $R^{2a}$ is as set forth herein.

In another embodiment of the invention, R¹ of formula (Ia), as set forth above, is

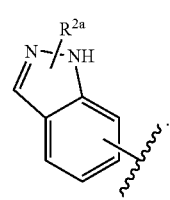

In another embodiment of the invention, $R^1$ of formula (Ia), as set forth above, is

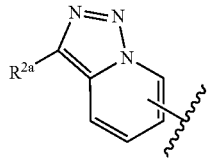

where $R^{2a}$ is as set forth herein.

In another embodiment of the invention, $R^1$ of formula (Ia), as set forth above, is

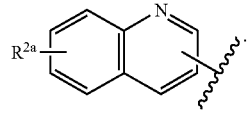

In another embodiment of the invention, $R^1$ of formula (Ia), as set forth above, is

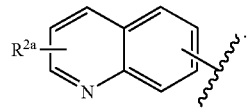

In another embodiment of the invention, $R^1$ of formula (Ia), as set forth above, is

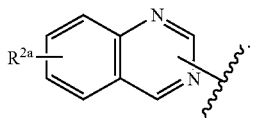

In another embodiment of the invention $R^1$ of formula (Ia), as set forth above, is

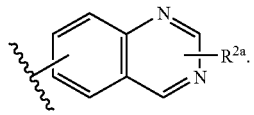

In another embodiment of the invention, $R^1$ of formula (Ia), as set forth above, is

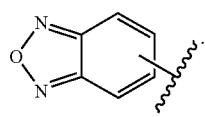

In another embodiment of the invention, $R^1$ of formula (Ia), as set forth above, is

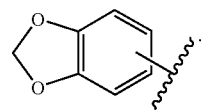

In another embodiment of the invention, $R^1$ of formula (Ia), as set forth above, is

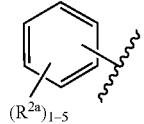

where $R^{2a}$ is as set forth herein and where the proviso language does not apply.

In another embodiment of the invention, $R^1$ of formula (Ia), as set forth above, is selected from the group consisting of:

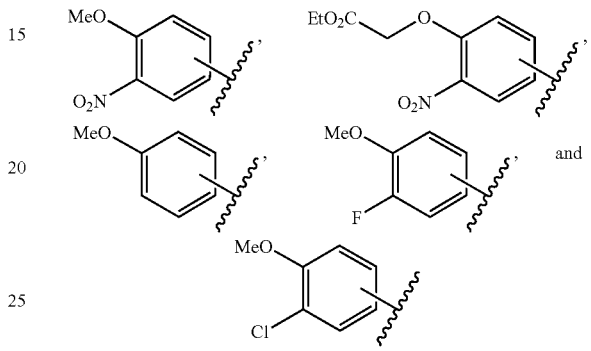

and where the proviso language does not apply.

In another embodiment of the invention $R^1$ of formula (Ia), as set forth above, is selected from the group consisting of:

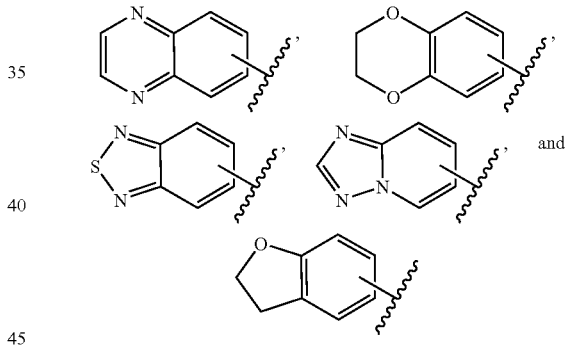

and where the proviso language does not apply.

In another embodiment of the invention, $R^1$ of formula (Ia), as set forth above, is selected from the group consisting of:

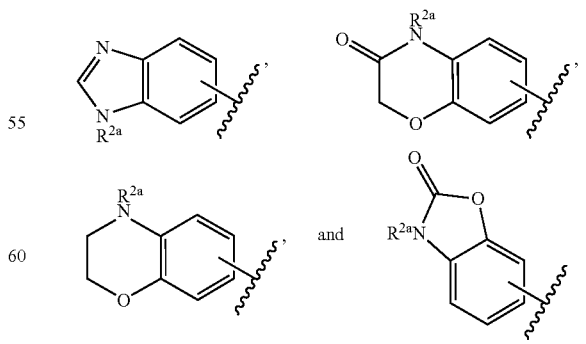

where $R^{2a}$ is as set forth herein and where the proviso language does not apply.

The invention also provides a pharmaceutical composition comprising at least one compound of the invention and a pharmaceutically acceptable carrier.

The invention further provides a method of preparation of a compound of the invention.

The invention still further provides a method of preventing or treating a TGF-related disease state in an animal or human comprising the step of administering a therapeutically effective amount of at least one compound of the invention to the animal or human suffering from the TGF-related disease state.

The invention still further provides the use of a compound of the invention in the preparation of a medicament for the prevention or treatment of a TGF-related disease state in an animal or human.

DEFINITIONS

As used herein, the article "a" or "an" refers to both the singular and plural form of the object to which it refers.

As used herein, the term "alkyl," as well as the alkyl moieties of other groups referred to herein (e.g., alkoxy) refers to a linear or branched saturated hydrocarbon (e.g. methyl, ethyl, n-propyl, isopropyl, n-butyl, iso-butyl, secondary-butyl, tertiary-butyl).

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl).

As used herein, the term "halogen" or "halo" refers to includes fluoro, chloro, bromo or iodo or fluoride, chloride, bromide or iodide.

As used herein, the term "halo-substituted alkyl" or "haloalkyl" refers to an alkyl radical, as set forth above, substituted with one or more halogens, as set forth above, including, but not limited to, chloromethyl, dichloromethyl, fluoromethyl, difluoromethyl, trifluoromethyl, and 2,2,2-trichloroethyl.

As used herein, the term "perhaloalkyl" refers to an alkyl radical, as set forth above, where each hyrdrogen of the alkyl group is replaced with a "halogen" or "halo", as set forth above.

As used herein, the term "alkenyl" refers to a linear or branched hydrocarbon chain radical containing at least two carbon atoms and at least one double bond. Examples include, but are not limited to, ethenyl, 1-propenyl, 2-propenyl (allyl), iso-propenyl, 2-methyl-1-propenyl, 1-butenyl, and 2-butenyl.

As used herein, the term "alkynyl" refers to a linear or branched hydrocarbon chain radical having at least one triple bond including, but not limited to, ethynyl, propynyl, and butynyl.

As used herein, the term "carbonyl" refers to a >C=O moiety. Alkoxycarbonylamino (i.e. alkoxy(C=O)—NH—) refers to an alkyl carbamate group. The carbonyl group is also equivalently defined herein as (C=O).

As used herein, the term "phenyl-[(alkyl)-N]-(C=O)—" refers to a N.N'-disubstituted amide group of the formula

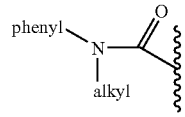

As used herein, the term "aryl" refers to an aromatic radical such as, for example, phenyl, naphthyl, tetrahydronaphthyl, and indanyl.

As used herein, the term "heteroaryl" refers to an aromatic group containing at least one heteroatom selected from O, S and N. For example, heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g. 1,2,3-triazolyl, 1,2,4-triazolyl), oxadiazolyl (e.g. 1,2,3-oxadiazolyl), thiadiazolyl (e.g. 1,3,4-thiadiazolyl), quinolyl, isoquinolyl, benzothienyl, benzofuryl, and indolyl.

As used herein, the term "heterocyclic" refers to a saturated or unsaturated $C_3$-$C_{20}$ mono-, bi- or polycyclic group containing at least one heteroatom selected from N, O, and S. Examples of heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxcithiazinyl, indolinyl, isoindolinyl, quincuclidinyl, chromanyl, isochromanyl, benzocazinyl, and the like. Examples of monocyclic saturated or unsaturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl.

As used herein, the term "pharmaceutically acceptable acid addition salt" refers to non-toxic acid addition salts, i.e., salts derived from pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

As used herein, the term "pharmaceutically acceptable base addition salt" refers to non-toxic base addition salts, i.e., salts derived from such pharmacologically acceptable cations such as alkali metal cations (e.g. potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

As used herein, the term "suitable substituent", "substituent", or "substituted" refers to a chemically and pharmaceutically acceptable functional group, i.e., a moiety that does not negate the inhibitory and/or therapeutic activity of the inventive compounds. Such suitable substituents may be routinely selected by those skilled in the art. Illustrative examples of suitable substituents include, but are not limited to, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, ester, amido, ether, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, arylsulfonyl and the like. Those skilled in the art will appreciate that many substituents can be substituted by additional substituents.

As used herein, the term "TGF-related disease state" refers to any disease state mediated by the production of TGF-β.

As used herein, the term "Ph" refers to phenyl.

As used herein, the term "a saturated, unsaturated, or aromatic $C_3$-$C_{20}$ mono-, bi- or polycyclic ring optionally containing at least one heteroatom" refers to, but is not limited to,

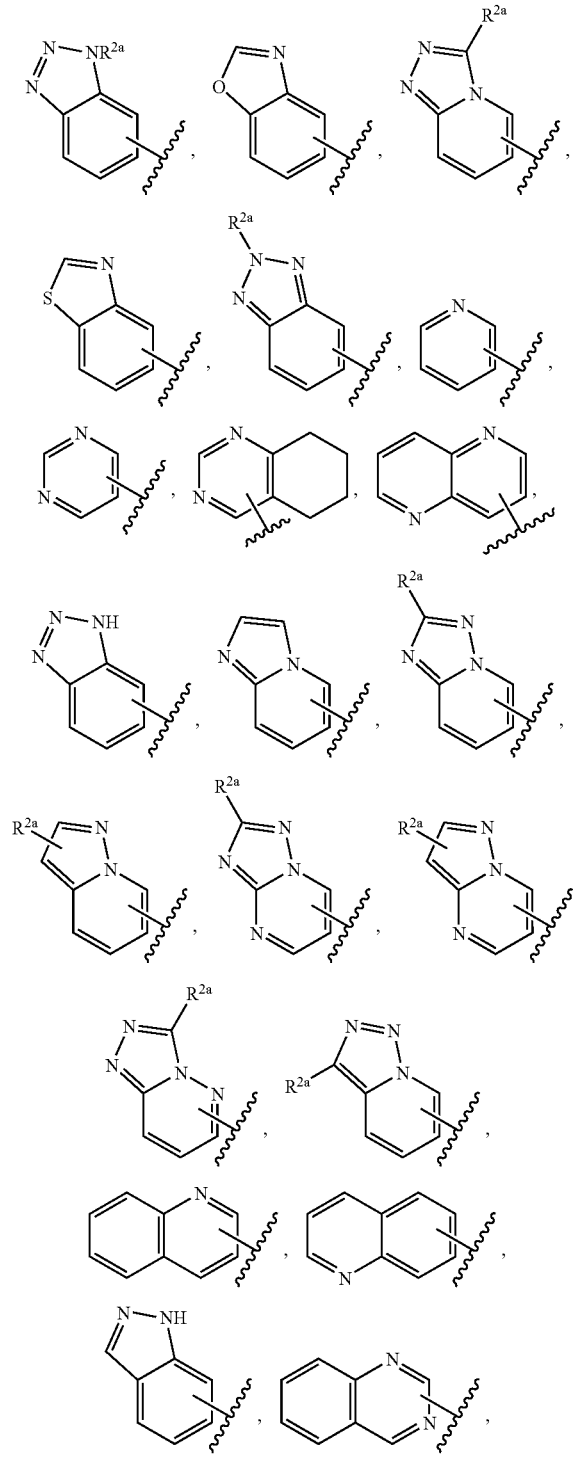

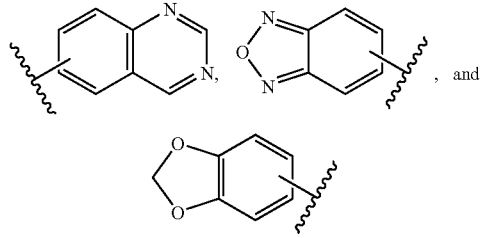

where $R^{2a}$ is independently selected from the group consisting of: $(C_1$-$C_6)$alkyl, $(C_2$-$C_6)$alkenyl, $(C_2$-$C_6)$alkynyl, $(C_3$-$C_{10})$cycloalkyl, $(C_5$-$C_{10})$aryl, $(C_1$-$C_6)$alkylaryl, amino, carbonyl, carboxyl, $(C_2$-$C_6)$acid, $(C_1$-$C_6)$ester, $(C_5$-$C_{10})$heteroaryl, $(C_5$-$C_{10})$heterocyclyl, $(C_1$-$C_6)$alkoxy, nitro, halo, hydroxyl, $(C_1$-$C_6)$alkoxy$(C_1$-$C_6)$ester, and those groups described in U.S. application Ser. Nos. 10/094,717, 10/094,760, and 10/115,952, each of which is herein incorporated in its entirety by reference; and where alkyl, alkenyl, alkynyl, cycloalkyl, aryl, amino, acid, ester, heteroaryl, heterocyclyl, and alkoxy of $R^{2a}$ is optionally substituted by at least one moiety independently selected from the group consisting of halo, $(C_1$-$C_6)$alkyl, $(C_2$-$C_6)$alkenyl, $(C_2$-$C_6)$alkynyl, perhalo $(C_1$-$C_6)$alkyl, phenyl, $(C_3$-$C_{10})$cycloalkyl, $(C_5$-$C_{10})$heteroaryl, $(C_5$-$C_{10})$heterocyclic, formyl, NC—, $(C_1$-$C_6)$alkyl-(C=O)—, phenyl-(C=O)—, HO—(C=O)—, $(C_1$-$C_6)$alkyl-O—(C=O)—, $(C_1$-$C_6)$alkyl-NH—(C=O)—, $((C_1$-$C_6)$alkyl)$_2$-N—(C=O)—, phenyl-NH—(C=O)—, phenyl-[$((C_1$-$C_6)$alkyl)-N]-(C=O)—, $O_2$N—, amino, $(C_1$-$C_6)$alkylamino, $((C_1$-$C_6)$alkyl)-2-amino, $(C_1$-$C_6)$alkyl-(C=O)—NH—, $(C_1$-$C_6)$alkyl-(C=O)-[$((C_1$-$C_6)$alkyl)-N]-, phenyl-(C=O)—NH—, phenyl-(C=O)-[$((C_1$-$C_6)$alkyl)-N]-, $H_2$N—(C=O)—NH—, $(C_1$-$C_6)$alkyl-HN—(C=O)—NH—, $((C_1$-$C_6)$alkyl)$_2$N—(C=O)—NH—, $(C_1$-$C_6)$alkyl-HN—(C=O)-[$((C_1$-$C_6)$alkyl)-N]-, $((C_1$-$C_6)$alkyl)$_2$N—(C=O)-[$(C_1$-$C_6)$alkyl-N]-, phenyl-HN—(C=O)—NH—, (phenyl)$_2$N—(C=O)—NH—, phenyl-HN—(C=O)-[$((C_1$-$C_6)$alkyl)-N]-, (phenyl-)$_2$N—(C=O)-[$((C_1$-$C_6)$alkyl)-N]-, $(C_1$-$C_6)$alkyl-O—(C=O)—NH—, $(C_1$-$C_6)$alkyl-O—(C=O)-[$((C_1$-$C_6)$alkyl)-N]-, phenyl-O—(C=O)—NH—, phenyl-O—(C=O)-[(alkyl)-N]-, $(C_1$-$C_6)$alkyl-SO$_2$NH—, phenyl-SO$_2$NH—, $(C_1$-$C_6)$alkyl-SO$_2$—, phenyl-SO$_2$—, hydroxy, $(C_1$-$C_6)$alkoxy, perhalo$(C_1$-$C_6)$alkoxy, phenoxy, $(C_1$-$C_6)$alkyl-(C=O)—O—, $(C_1$-$C_6)$ester-$(C_1$-$C_6)$alkyl-O—, phenyl-(C=O)—O—, $H_2$N—(C=O)—O—, $(C_1$-$C_6)$alkyl-HN—(C=O)—O—, $((C_1$-$C_6)$alkyl)$_2$N—(C=O)—O—, phenyl-HN—(C=O)—O—, and (phenyl)$_2$N—(C=O)—O—.

DETAILED DESCRIPTION OF THE INVENTION

The following reaction schemes illustrate the preparation of the compounds of the present invention. A compound of the invention may be prepared by methods analogous to those described in U.S. application Ser. Nos. 10/094,717, 10/094,760, and 10/115,952 and WO 02/40476. Unless otherwise indicated, $R^1$, $R^3$, $R^4$, $R^6$, $R^{2a}$ and s in the reaction schemes and the discussion that follow are defined above.

SCHEME 1

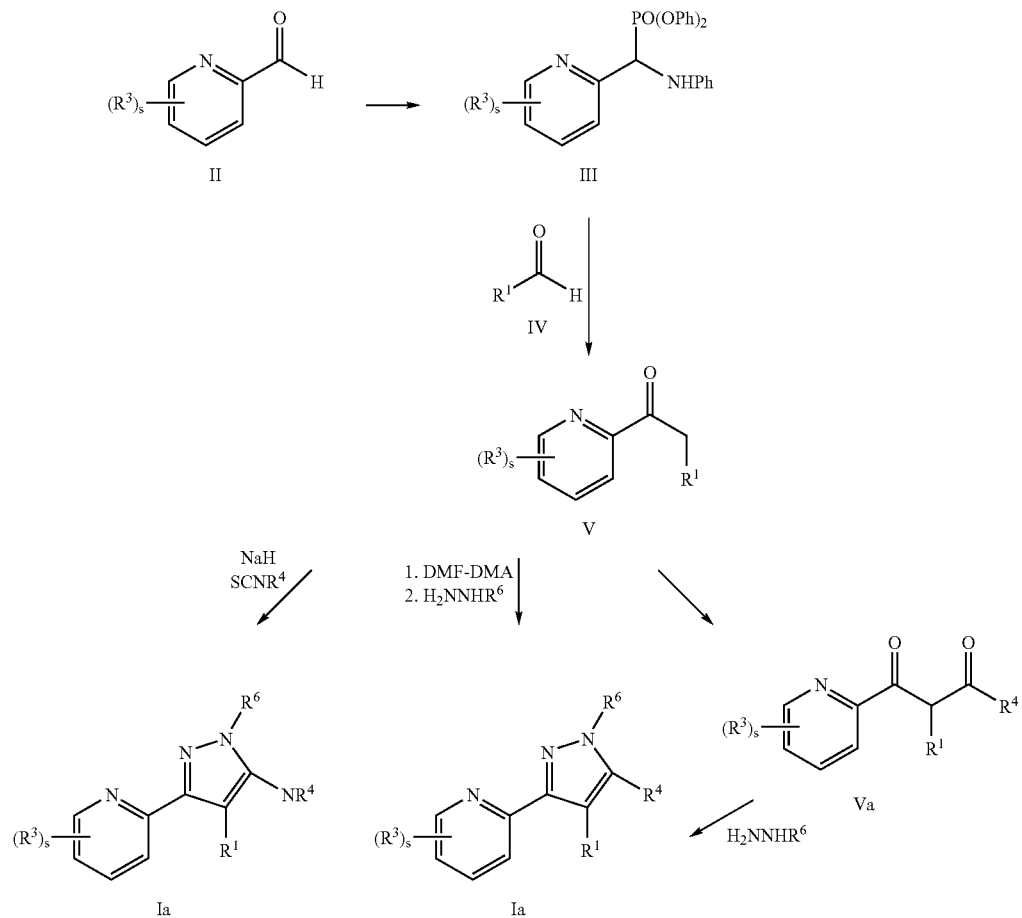

Scheme 1 refers to the preparation of compounds of the formula Ia. Referring to Scheme 1, a compound of the formula III was prepared from aldehydes of the formula II by first treatment with an aromatic amine, such as aniline, in a polar solvent. Suitable solvents include ethyl acetate, isopropyl acetate, or tetrahydrofuran, preferably isopropyl acetate. The resulting reaction mixture is heated to a temperature from about 50° C. to about 100° C., preferably about 60° C., and then slowly treated with phosphorous acid diphenyl ester. The temperature of the reaction mixture was maintained for a period from about 30 minutes to about 3 hours, preferably about 1 hour and then cooled to ambient temperature overnight. A compound of formula II was prepared according to Preparation E, set forth below.

A compound of the formula V was prepared from a compound of the formula III by reaction with an aldehyde of the formula IV in the presence of a base, such as potassium tert-butoxide, in a polar solvent. Suitable solvents include ethyl acetate, isopropyl acetate, or tetrahydrofuran, preferably a mixture of tetrahydrofuran and isopropyl acetate. The aforesaid reaction was run at a temperature from about 0° C. to about 100° C., preferably about 22° C. (ambient temperature), for a period from about 30 minutes to about 5 hours, preferably about 2 hours. The resulting reaction mixture was then treated with acid, such as hydrochloric acid, for a period from about 30 minutes to about 5 hours, preferably about 1 hour.

A compound of formula Ia was prepared from a compound of formula V by treatment with an excess of dimethylformamide dimethylacetal, DMF-DMA, and heating neat at a temperature from about 60° C. to about 100° C., preferably about 80° C., for a period of about 30 minutes to about 4 hours, preferably about 2 hours. Following removal of the excess dimethylformamide dimethylacetal, an appropriate hydrazine, such as $H_2NNHR^6$, in a polar solvent was added. Suitable solvents for the aforesaid reaction include methanol and ethanol. The aforesaid reaction was conducted at temperature of about 0° C. to about 50° C., preferably about 22° C. (ambient temperature), for about 1 to about 4 hours, preferably about 2 hours.

Alternatively, a compound of formula Va can be prepared from a compound of formula V by reaction with a base such as lithium bis(trimethylsilyl)amide in a solvent such as tetrahydrofuran at a temperature of −78° C. followed by addition of a simple ester of activated carboxylic acid ($R^4CO_2H$) such as an acid chloride or acyl imidazole. A compound of formula Ia is then formed by addition of an appropriate hydrazine, such as $H_2NNHR^6$ Alternatively, a compound of formula Ia can be prepared by treatment of V with a base such as sodium hydride in a solvent such as pyridine followed by addition of a thioisocyanate, SCNR⁴. A compound of formula Ia is then formed by addition of an appropriate hydrazine, such as $H_2NNHR^6$.

Alternatively, a compound of formula Ia can be prepared according to the procedures set forth in WO 00/31063 and WO 02/72576.

SCHEME 2

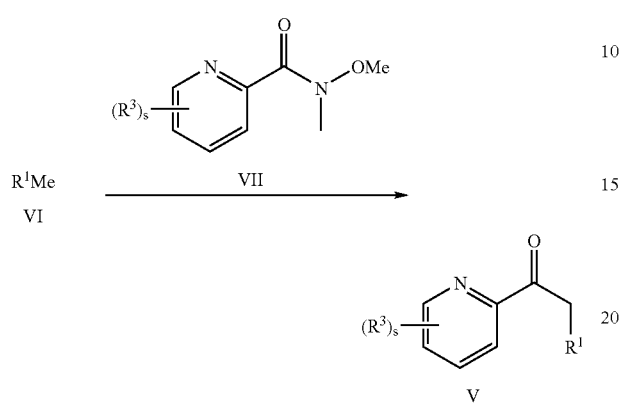

Scheme 2 refers to the preparation of compounds of the formula V, which are intermediates in the preparation of compounds of formula Ia in Scheme 1. Referring to Scheme 2, a compound of the formula V was prepared from a compound of the formula VI by treatment with a base, such as butyl lithium, at a temperature of about −60° C. for a time period of about 90 minutes, followed by the slow addition of pyridyl amide of the formula VII, which is either commercially available or prepared according to methods analogous to those of Preparation C, as set forth below, where $R^1$ is replaced by

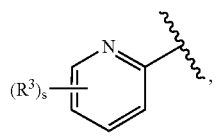

in a polar aprotic solvent, such as tetrahydrofuran. The aforesaid reaction was run at a temperature from about −78° C. to about 0° C., preferably about −20° C., for a period from about 1 hour to about 10 hours, preferably about 3 hours.

Alternatively the compound of formula V can be prepared according to the methods of Davies, I. W.; Marcoux, J. F.; Corley, E. G.; Journet, M.; Cai, D.-W.; Palucki, M.; Wu, J.; Larsen, R. D.; Rossen, K.; Pye, P. J.; DiMichele, L.; Dormer, P.; Reider, P. J.; *J. Org. Chem.*, Vol. 65, pp. 8415-8420 (2000).

SCHEME 3

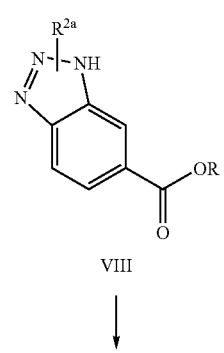

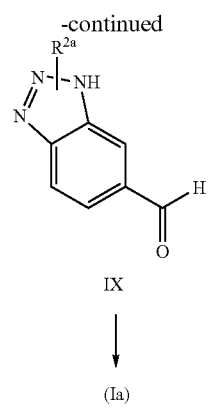

Scheme 3 refers to the preparation of compounds of the formula Ia where $R^1$ is

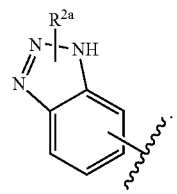

Referring to Scheme 3, compounds of the formula IX were prepared from compounds of the formula VIII according to the procedure for the conversion of compound XII to compound IV described in Preparation A, as set forth below. Compounds of formula VIII were prepared according to Preparation D, set forth below. In Scheme 3 the compound of formula Ia can be prepared from compound IX according to procedures described in Scheme 1.

SCHEME 4

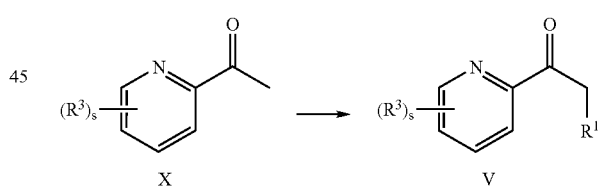

Scheme 4 refers to the preparation of compounds of the formula V, which are intermediates in the preparation of compounds of formula Ia in Scheme 1. Referring to Scheme 4, a compound of the formula V was prepared from compound of the formula X, which is either commercially available or prepared according to Preparation B, as set forth below, by reaction with a compound of the formula $R^1$—Cl, in the presence of a catalyst such as palladium II acetate, a base (e.g. potassium tert-butoxide, and AMPHOS® (i.e., 2-dicyclohexylphosphino-2'-(N,N-dimethylamino)biphenyl, commercially available from Strem Chemicals, Newburyport, Mass.)) in a polar aprotic solvent such as tetrahydrofuran. The aforesaid reaction was run at a temperature from about 50° C. to about 100° C., preferably about 75° C., for a period from about 6 hours to about 24 hours, preferably about 18 hours.

Preparation A

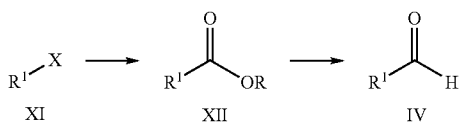

Preparation A refers to the preparation of compounds of the formula IV, which are intermediates useful in the preparation of compounds of the formula Ia. In Preparation A, R is a simple alkyl group such as methyl or ethyl. Referring to Preparation A, compounds of the formula XII were prepared from a compound of the formula XI, wherein X is a chloride or bromide, by an alkoxycarbonylation reaction. Suitable conditions include metal-halogen exchange with butyl lithium in a solvent such as tetrahydrofuran at a temperature of about 0° C., for a period of time of about 30 minutes, followed by the addition of ethylchloroformate at a temperature of about 0° C., followed by a period of time of about 2.4 hours at about 50° C. A compound of formula XI is commercially available.

The compound of the formula IV was prepared from a compound of the formula XII by a two-step process. First the compound of formula XII was treated with a reducing agent. Suitable reducing agents include lithium borohydride, sodium borohydride, lithium aluminum hydride, and borane in tetrahydrofuran. Suitable solvents for the aforesaid reaction include methanol, ethanol, tetrahydrofuran, diethyl ether, and dioxane. The aforesaid reaction was run at a temperature from about 0° C. to about 100° C., preferably about 65° C., for a period from about 10 minutes to about 1 hour, preferably about 30 minutes. The resulting primary alcohol was then oxidized to the corresponding aldehyde of the formula IV by treatment with an oxidizing agent, such as N-methyl morpholine N-oxide/TPAP, Dess-Martin reagent, PCC or oxalyl chloride-DMSO, preferably oxalyl chloride-DMSO. Suitable solvents for the aforesaid reaction include chloroform, tetrahydrofuran, or dichloromethane. The aforesaid reaction was conducted at a temperature from about −78° C. to about 22° C. for a time from about 15 minutes to about 3 hours, preferably about 1 hour.

Preparation B

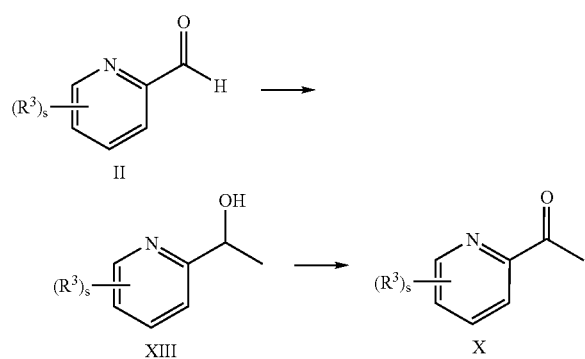

Preparation B refers to the preparation of compounds of the formula X, which are intermediates useful in the preparation of compounds of the formula Ia. Referring to Preparation B, a compound of formula XIII was prepared from a compound of the formula II by reaction with methyl magnesium bromide in a polar solvent such as a mixture of tetrahydrofuran and toluene. The aforesaid reaction was run at a temperature from about −78° C. to about 0° C., preferably about −60° C., for a period from about 10 minutes to about 1 hour, preferably about 40 minutes, followed by a period of about 90 minutes at a temperature of about −10° C. The compound of formula II was prepared according to Preparation E, set forth below.

The compound of formula X was prepared from a compound of the formula XIII by treatment with an oxidizing agent, such as N-methyl morpholine N-oxide/TPAP, Dess-Martin reagent, PCC or oxalyl chloride-DMSO, preferably oxalyl chloride-DMSO. Suitable solvents for the aforesaid reaction include chloroform, tetrahydrofuran, or dichloromethane. The aforesaid reaction was conducted at a temperature from about −78° C. to about 22° C. for a time from about 15 minutes to about 3 hours, preferably about 1 hour.

Preparation C

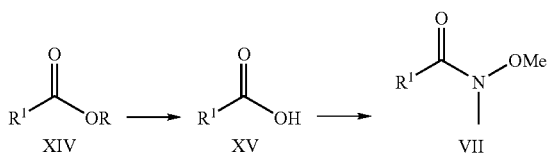

Preparation C refers to the preparation of compounds of the formula VII, which are intermediates useful in the preparation of compounds of the formula Ia. In Preparation C, R is a simple alkyl group such as methyl or ethyl. Referring to Preparation C, compounds of the formula XV were prepared from a compound of the formula XIV, which may be prepared according to a procedure described in Preparation A or are commercially available, by treatment with a base such as lithium hydroxide, in a polar protic solvent. Suitable solvents for the aforesaid reaction included methanol, ethanol, and water. The aforesaid reaction was conducted at a temperature from about 0° C. to about 30° C. preferably about 22° C. (room temperature) for a time from about 15 minutes to about 3 hours, preferably about 1 hour.

The compound of the formula VII was prepared from a compound of the formula XV by reaction with a suitable activating agent and a compound of the formula

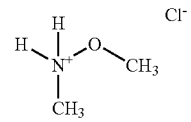

and a base. Suitable activating agents included thionyl chloride, carbonyldiimidazole, EDCI and DCC, preferably oxalyl chloride. Suitable bases included triethylamine, Hunig's base, or DBU, preferably triethylamine. Suitable solvents for the aforesaid reaction include methylene chloride, N,N'-dimethylformamide, tetrahydrofuran, and a mixture thereof, preferably methylene chloride. The aforesaid reaction was conducted at a temperature from about 0° C. to about 30° C., preferably about 22° C. (room temperature) for a time from about 6 hours to about 48 hours, preferably about 12 hours.

Preparation D

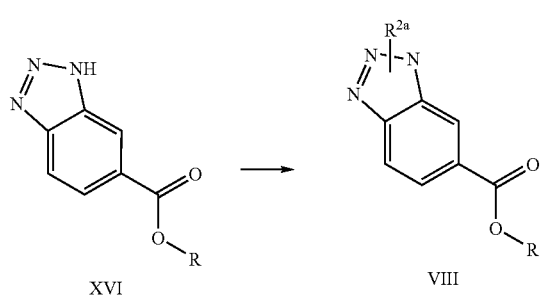

Preparation D refers to the preparation of compounds of the formula VIII, which is an intermediate useful in the preparation of compounds of formula (Ia), where $R^1$ is

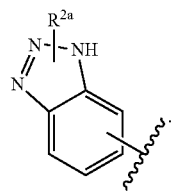

In Preparation D, R is $(C_1-C_6)$alkyl. The compound of formula VIII was prepared from a compound of formula XVI by treatment with an alkyl halide, such as methyl iodide, in the presence of a base such as sodium hydride, in a polar aprotic solvent such as N,N'-dimethylformamide. Compounds of the formula XVI are commercially available.

Preparation E

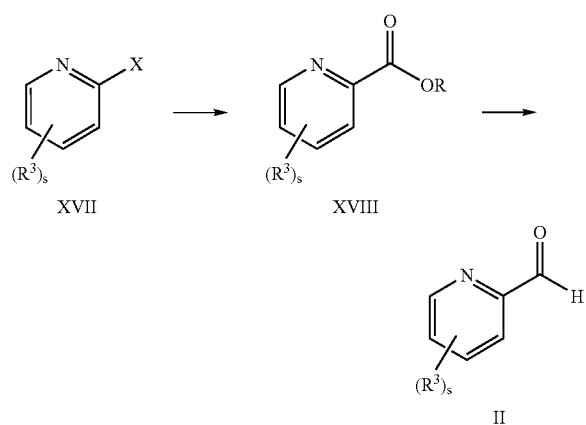

Preparation E refers to the preparation of compounds of the formula II, which are intermediates useful in the preparation of compounds of formula (Ia). In Preparation E, R is a simple alkyl group such as methyl or ethyl. Referring to Preparation E, compounds of the formula XVIII were prepared from heteroarylhalides of the formula XVII, wherein X is a chloride or bromide, according to the procedure described for the preparation of compound XII from compound XI in Preparation A.

The compound of the formula II was prepared from a compound of the formula XVIII according to the two-step process described for the preparation of compound IV from compound XII in Preparation A.

Preparation F

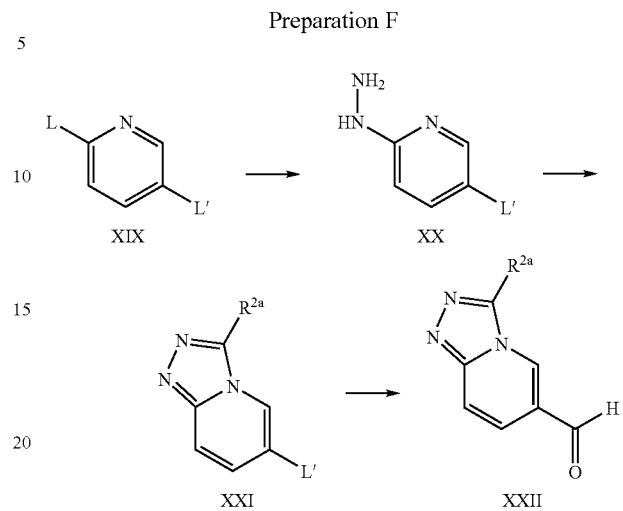

Preparation F refers to the preparation of compounds of the formula XXII which are intermediates in the preparation of compounds of the formula (Ia). Referring to preparation F, compounds of formula XXII were prepared from compounds of formula XXI by a formylation reaction. Suitable conditions for formylation include metal halogen exchange with isopropylmagnesium chloride in a solvent such as tetrahydrofuran at a temperature of about 0° C., for a period of time of about 30 minutes, followed by the addition of N,N-dimethylformamide at a temperature of about 0° C., followed by a period of time of about 2.5 hours at a temperature of about 50° C.

Compounds of formula XX were prepared as described in the literature (Moran, D. B.; Morton, G. O.; Albright, J. D., *J. Heterocycl. Chem.*, Vol. 23, pp. 1071-1077 (1986)) or from compounds of formula XIX wherein L and L', which can be the same or different, are chloride, bromide or iodide, by reaction with hydrazine. A compound of formula XXI was prepared from a compound of formula XX by condensation of compound XX with a cyclization reagent such as acid chloride, acid anhydride, trialkylorthoacetate or trialkylorthoformate. Compounds of formula XIX are commercially available.

All pharmaceutically acceptable salts, prodrugs, tautomers, hydrates and solvates of a compound of the invention is also encompassed by the invention.

A compound of the invention which is basic in nature is capable of forming a wide variety of different salts with various inorganic and organic acids. Although such salts must be pharmaceutically acceptable for administration to animals and humans, it is often desirable in practice to initially isolate a compound of the invention from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

The acids which can be used to prepare the pharmaceutically acceptable acid addition salts of the base compounds of this invention are those which form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

A compound of the invention which is also acidic in nature, e.g. contains a COOH or tetrazole moiety, is capable of forming base salts with various pharmacologically acceptable cations. Although such salts must be pharmaceutically acceptable for administration to animals and humans, it is often desirable in practice to initially isolate a compound of the invention from the reaction mixture as a pharmaceutically unacceptable salt and then simply convert the latter back to the free acid compound by treatment with an acidic reagent, and subsequently convert the free acid to a pharmaceutically acceptable base addition salt. Examples of such pharmaceutically acceptable base addition salts include the alkali metal or alkaline-earth metal salts and particularly, the sodium and potassium salts. These salts can be prepared by conventional techniques. The chemical bases which can be used as reagents to prepare the pharmaceutically acceptable base addition salts of this invention are those which form non-toxic base salts with the herein described acidic compounds of the invention. These non-toxic base salts include salts derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Isotopically-labeled compounds are also encompassed by the present invention. As used herein, an "isotopically-labeled compound" refers to a compound of the invention including pharmaceutical salts, prodrugs thereof, each as described herein, in which one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling a compound of the present invention, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds of the invention, including pharmaceutical salts, prodrugs thereof, can be prepared by any means known in the art.

Stereoisomers (e.g. cis and trans isomers) and all optical isomers of a compound of the invention (e.g. R and S enantiomers), as well as racemic, diastereomeric and other mixtures of such isomers are contemplated by the present invention.

The compounds, salts, prodrugs, tautomers, hydrates, and solvates of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the present invention. Atropisomers refer to compounds of the invention that can be separated into rotationally restricted isomers.

A compound of the invention, as described above, can be used in the manufacture of a medicament for the prophylactic or therapeutic treatment of a TGF-related disease state in an animal or human.

A compound of the invention is a potent inhibitor of transforming growth factor ("TGF")-β signaling pathway and are therefore of use in therapy. Accordingly, the present invention provides a method of preventing or treating a TGF-related disease in an animal or human comprising the step of administering a therapeutically effective amount of at least one compound of the invention to the animal or human suffering from the TGF-related disease state.

As used herein, the term "therapeutically effective amount" refers to an amount of a compound of the invention required to inhibit the TGF-β signaling pathway. As would be understood by one of skill in the art, a "therapeutically effective amount" will vary from patient to patient and will be determined on a case by case basis. Factors to consider include, but are not limited to, the patient being treated, weight, health, compound administered, etc.

There are numerous disease states that can be treated by inhibition of the TGF-β signaling pathway. Such disease states include, but are not limited to, all types of cancer (e.g., breast, lung, colon, prostate, ovarian, pancreatic, melanoma, all hematological malignancies, etc.) as well as all types of fibrotic diseases (e.g., glomerulonephritis, diabetic nephropathy, hepatic fibrosis, pulmonary fibrosis, arterial hyperplasia and restenosis, scleroderma, and dermal scarring).

The present invention also provides a pharmaceutical composition comprising at least one compound of the invention and at least one pharmaceutically acceptable carrier. The pharmaceutically acceptable carrier may be any such carrier known in the art including those described in, for example, Remington's Pharmaceutical Sciences, Mack Publishing Co., (A. R. Gennaro edit. 1985). A pharmaceutical composition of the invention may be prepared by conventional means known in the art including, for example, mixing at least one compound of the invention with a pharmaceutically acceptable carrier.

A pharmaceutical composition of the invention may be used in the prevention or treatment of a TGF-related disease state, as described above, in an animal or human. Thus, a compound of the invention may be formulated as a pharmaceutical composition for oral, buccal, intranasal, parenteral (e.g., intravenous, intramuscular or subcutaneous), topical, or rectal administration or in a form suitable for administration by inhalation or insufflation.

For oral administration, the pharmaceutical composition may take the form of, for example, a tablet or capsule prepared by conventional means with a pharmaceutically acceptable excipient such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g. potato starch or sodium starch glycolate); or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and preservative (e.g., methyl or propyl p-hydroxybenzoates or sorbic acid).

For buccal administration, the composition may take the form of tablets or lozenges formulated in conventional manner.

A compound of the present invention may also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

A compound of the invention may be formulated for parenteral administration by injection, including using conventional catheterization techniques or infusion. Formulations for injection may be presented in unit dosage form, e.g. in ampules or in multi-dose containers, with an added preservative. The compositions may take such forms as suspensions, solutions or emulsions in oily or aqueous vehicles, and may contain a formulating agent such as a suspending, stabilizing and/or dispersing agent. Alternatively, the active ingredient may be in powder form for reconstitution with a suitable vehicle, e.g., sterile pyrogen-free water, before use.

A compound of the invention may also be formulated in rectal compositions such as suppositories or retention enemas, e.g., containing conventional suppository bases such as cocoa butter or other glycerides.

For intranasal administration or administration by inhalation, a compound of the invention may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the compound of the invention. Capsules and cartridges (made, for example, from gelatin) for use in an inhaler or insufflator may be formulated containing a powder mix of a compound of the invention and a suitable powder base such as lactose or starch.

A proposed dose of a compound of the invention for oral, parenteral or buccal administration to the average adult human for the treatment of a TGF-related disease state is about 0.1 mg to about 2000 mg, preferably, about 0.1 mg to about 200 mg of the active ingredient per unit dose which could be administered, for example, 1 to 4 times per day.

Aerosol formulations for treatment of the conditions referred to above in the average adult human are preferably arranged so that each metered dose or "puff" of aerosol contains about 20 µg to about 10,000 µg, preferably, about 20 µg to about 1000 µg of a compound of the invention. The overall daily dose with an aerosol will be within the range from about 100 µg to about 100 mg, preferably, about 100 µg to about 10 mg. Administration may be several times daily, for example 2, 3, 4 or 8 times, giving for example, 1, 2 or 3 doses each time.

Aerosol combination formulations for treatment of the conditions referred to above in the average adult human are preferably arranged so that each metered dose or "puff" of aerosol contains from about 0.01 mg to about 1000 mg, preferably, about 0.01 mg to about 100 mg of a compound of this invention, more preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 20,000 mg, preferably, about 0.01 mg to about 2000 mg of a compound of the invention, more preferably from about 1 mg to about 200 mg. Administration may be several times daily, for example 2, 3, 4 or 8 times, giving for example, 1, 2 or 3 doses each time.

For topical administration, a compound of the invention may be formulated as an ointment or cream.

This invention also encompasses pharmaceutical compositions containing and methods of treatment or prevention comprising administering prodrugs of at least one compound of the invention. As used herein, the term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs. Prodrugs include compounds wherein an amino acid residue, or a polypeptide chain of two or more (e.g. two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain.

According to the invention, in the treatment of a TGF-related disease state, a compound of the invention, as described herein, whether alone or as part of a pharmaceutical composition may be combined with another compound(s) of the invention and/or with another therapeutic agent(s). Examples of suitable therapeutic agent(s) include, but are not limited to, standard non-steroidal anti-inflammatory agents (hereinafter NSAID's) (e.g, piroxicam, diclofenac), propionic acids (e.g., naproxen, flubiprofen, fenoprofen, ketoprofen and ibuprofen), fenamates (e.g., mefenamic acid, indomethacin, sulindac, apazone), pyrazolones (e.g., phenylbutazone), salicylates (e.g., aspirin), COX-2 inhibitors (e.g., celecoxib, valdecoxib, rofecoxib and etoricoxib), analgesics and intraarticular therapies (e.g., corticosteroids) and hyaluronic acids (e.g., hyalgan and synvisc), anticancer agents (e.g., endostatin and angiostatin), cytotoxic drugs (e.g., adriamycin, daunomycin, cis-platinum, etoposide, taxol, taxotere), alkaloids (e.g., vincristine), and antimetabolites (e.g., methotrexate), cardiovascular agents (e.g., calcium channel blockers), lipid lowering agents (e.g., statins), fibrates, beta-blockers, Ace inhibitors, Angiotensin-2 receptor antagonists and platelet aggregation inhibitors, CNS agents (e.g., as antidepressants (such as sertraline)), anti-Parkinsonian drugs (e.g., deprenyl, L-dopa, Requip, Mirapex), MAOB inhibitors (e.g., selegine and rasagiline), comP inhibitors (e.g., Tasmar), A-2 inhibitors, dopamine reuptake inhibitors, NMDA antagonists, Nicotine agonists, Dopamine agonists and inhibitors of neuronal nitric oxide synthase), anti-Alzheimer's drugs (e.g., donepezil, tacrine, COX-2 inhibitors, propentofylline or metryfonate), osteoporosis agents (e.g., roloxifene, droloxifene, lasofoxifene or fosomax), and immunosuppressant agents (e.g., FK-506 and rapamycin).

Biological Activity

The activity of the compounds of the invention for the various TGF-related disease states as described herein can be determined according to one or more of the following assays. According to the invention, a compound of the invention exhibits an in vitro $IC_{50}$ value of less than about 10 μM. For example, the compound of Example 7 exhibits a TβRI $IC_{50}$ value of about 51 nM.

The compounds of the present invention also possess differential activity (i.e. are selective for) for TβRI over TβRII and TβRIII. Selectivity is measured in standard assays as a $IC_{50}$ ratio of inhibition in each assay.

TGF-β Type II Receptor (TβRII) Kinase Assay Protocol

Phosphorylation of myelin basic protein (MBP) by the TβRII kinase was measured as follows: 80 microliters of MBP (Upstate Biotechnology #13-104) diluted in kinase reaction buffer (KRB) containing 50 mM MOPS, 5 mM $MgCl_2$, pH 7.2 to yield a final concentration of 3 micromolar MBP was added to each well of a Millipore 96-well multiscreen-DP 0.65 micron filtration plate (#MADPNOB50). 20 microliters of inhibitor diluted in KRB was added to appropriate wells to yield the desired final concentration (10-0.03 micromolar). 10 microliters of a mixture of ATP (Sigma #A-5394) and $^{33}$P-ATP (Perkin Elmer #NEG/602H) diluted in KRB was added to yield a final concentration of 0.25 micromolar ATP and 0.02 microcuries of $^{33}$P-ATP per well. 10 microliters of a GST-TβRII fusion protein (glutathione S-transferase at the N-terminal end of the cytoplasmic domain of TβRII-amino acids 193-567 with A to V change at 438) diluted in KRB was added to each well to yield a final concentration of 27 nanomolar GST-TβRII. Plates were mixed and incubated for 90 minutes at room temperature. After the reaction incubation, 100 microliters of cold 20% trichloroacetic acid (Aldrich #25, 139-9) was added per well and plates were mixed and incubated for 60 minutes at 4° C. Liquid was then removed from the wells using a Millipore vacuum manifold. Plates were washed once with 200 microliters per well of cold 10% trichloroacetic acid followed by two washes with 100 microliters per well of cold 10% trichloroacetic acid. Plates were allowed to dry overnight at room temperature. 20 microliters of Wallac OptiPhase SuperMix scintillation cocktail was added to each well. Plates were sealed and counted using a Wallac 1450 Microbeta liquid scintillation counter. The potency of inhibitors was determined by their ability to reduce TβRII-mediated phosphorylation of the MBP substrate.

ALK-5 (TβRI) Kinase Assay Protocol

The kinase assays were performed with 65 nM GST-ALK5 and 84 nM GST-Smad3 in 50 mM HEPES, 5 mM $MgCl_2$, 1 mM $CaCl_2$, 1 mM dithiothreitol, and 3_M ATP. Reactions were incubated with 0.5_Ci of [33 P]_ATP for 3 h at 30° C. Phosphorylated protein was captured on P-81 paper (Whatman, Maidstone, England), washed with 0.5% phosphoric acid, and counted by liquid scintillation. Alternatively, Smad3 or Smad1 protein was also coated onto FlashPlate Sterile Basic Microplates (PerkinElmer Life Sciences, Boston, Mass.). Kinase assays were then performed in FlashPlates with same assay conditions using either the kinase domain of ALK5 with Smad3 as substrate or the kinase domain of ALK6 (BMP receptor) with Smad1 as substrate. Plates were washed three times with phosphate buffer and counted by TopCount (Packard Bio-science, Meriden, Conn.). (Laping, N. J. et al. *Molecular Pharmacology* 62:58-64 (2002)).

The following Examples illustrate the preparation of the compounds of the present invention. Melting points are uncorrected. NMR data are reported in parts per million (d) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonirile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 AMU to 1100 AMU. Specific rotations were measured at room temperature using the sodium D line (589 nm). Commercial reagents were utilized without further purification. THF refers to tetrahydrofuran. DMF refers to N,N- dimethylformamide. Chromatography refers to column chromatography performed using 32-63 mm silica gel and executed under nitrogen pressure (flash chromatography) conditions. Room or ambient temperature refers to 20-25° C. All non-aqueous reactions were run under a nitrogen atmosphere for convenience and to maximize yields. Concentration at reduced pressure means that a rotary evaporator was used.

One of ordinary skill in the art will appreciate that in some cases protecting groups may be required during preparation. After the target molecule is made, the protecting group can be removed by methods well known to those of ordinary skill in the art, such as described in Greene and Wuts, "*Protective Groups in Organic Synthesis*" ($2^{nd}$ Ed, John Wiley & Sons 1991).

Analytical high performance liquid chromatography on reverse phase with mass spectrometry detection (LSMS) was done using Polaris 2×20 mm $C_{18}$ column. Gradient elution was applied with increase of concentration of acetonitrile in 0.01% aqueous formic acid from 5% to 100% during 3.75 min period. Mass spectrometer Micromass ZMD was used for molecular ion identification.

EXAMPLE 1

Preparation of 4-[3-(6-Methyl-pyridyl-2-yl)-1H-pyrazol-4-yl-quinoline

Step A: Preparation of F(6-Methyl-pyridyl-2-yl)-phenylamino-methyl]-phosphonic Acid Diphenyl Ester A 2 L round-bottom flask was charged with 6-methyl-pyridine-2-carbalydehyde (40 g, 330 mmol), aniline (30.1 mL, 330 mmol), and 380 mL of isopropyl acetate. The reaction mixture was heated to 65° C. and diphenylphosphite (112 mL, 495 mmol) was added dropwise over 60 minutes. The mixture was stirred an additional 60 minutes at 65° C., then at room temperature overnight. Concentration in vacuo yielded a syrup that was dissolved in 1 liter of ethyl acetate and washed with saturated sodium bicarbonate (3×200 mL). The organic layer was dried over sodium sulfate, filtered and concentrated onto silica gel. Product was purified by flash chromatography using 10-20% ethylacetate/hexane solvent gradient to afford 126.5 grams of pure material. HPLC $t_R$=6.68 min, LC-MS=431 (M+1).

Step B: Preparation of 1-(6-Methyl-pyridyl-2-yl)-2-quinolin-4-yl-ethanone

A 2 L round-bottom flask was charged with [(6-Methyl-pyridyl-2-yl)-phenylamino-methyl]-phosphonic acid diphenyl ester (24.5 g, 57 mmol), quinoline-4-carbaldehyde (11.65 g, 74.1 mmol), 90 mL of tetrahydrofuran, and 180 mL of isopropylalcohol. The reaction mixture was warmed to 25° C. and potassium t-butoxide (1.0M, 74.1 mL, 74.1 mmol) was added dropwise over 90 minutes. After stirring an additional 30 minutes, hydrochloric acid (2M, 122 mL) was added and the mixture stirred one hour. The solution was heated to 45° C. and the pH was adjusted to 5 with 6M sodium hydroxide, stirred an additional hour, then concentrated in vacuo. The residue was dissolved in chloroform and concentrated onto silica gel. Product was purified by flash chromatography using 0-10% ethylacetate/hexane solvent gradient to afford 10.97 grams of pure material. HPLC $t_R$=5.02 min, LC-MS=263 (M+1).

Step C: Preparation of 4-[3-(6-Methyl-pyridyl-2-yl)-1H-pyrazol-4-yl-quinoline

A 500 mL round-bottom flask was charged with 1-(6-Methyl-pyridyl-2-yl)-2-quinolin-4-yl-ethanone (5.0 g, 19 mmol) and N,N-dimethylformamide dimethyl acetal (40.4 mL, 304 mmol) and heated to 80 C. After 2 hours, the solution was concentrated in vacuo and 68 mL of ethanol was added followed by hydrazine hydrate (6.74 mL, 108 mmol). The mixture was stirred an additional 2 hours then concentrated to dryness. Chromatography on silica gel with 20-60% ethylacetate/chloroform afforded 3.26 grams of the desired product. HPLC $t_R$=3.94 min, LC-MS=287 (M+1).

EXAMPLE 2

2-(4-Benzo[1,3]dioxol-5-yl-1H-pyrazol-3-yl)-6-methyl-pyridine

The title compound was prepared according to procedures analogous to those described in Example 1. HPLC $t_R$=4.38 min, LC-MS=280 (M+1).

EXAMPLE 3

1-Methyl-6-[3-(6-methyl-pyridin-2-yl)-1H-pyrazol-4-yl]-1H-benzotriazole

The title compound was prepared according to procedures analogous to those described in Example 1. HPLC $t_R$=3.52 min, LC-MS=291 (M+1).

EXAMPLE 4

4-(3-Pyridin-2-yl-1H-pyrazol-4-yl)-quinoline

The title compound was prepared according to procedures analogous to those described in Example 1. HPLC $t_R$=3.6 min, LC-MS=273 (M+1).

EXAMPLE 5

2-(4-Benzo[1,3]dioxol-5-yl-1-methyl-1H-pyrazol-3-yl)-6-methyl-pyridine

The title compound was prepared according to procedures analogous to those described in Example 1. HPLC $t_R$=4.45 min, LC-MS=294 (M+1).

EXAMPLE 6

4-[1-Methyl-3-(6-methyl-pyridin-2-yl)-1H-pyrazol-4-yl]-quinoline

The title compound was prepared according to procedures analogous to those described in Example 1. HPLC $t_R$=4.17 min, LC-MS=301 (M+1).

EXAMPLE 7

2-(4-Benzo[1,3]dioxol-5-yl-1H-pyrazol-3-yl)-pyridine

The title compound was prepared according to procedures analogous to those described in Example 1. HPLC $t_R$=4.18 min, LC-MS=266 (M+1).

EXAMPLE 8

2-[4-(2,3-Dihydro-benzo[1,4]dioxin-6-yl)-1H-pyrazol-3-yl]-pyridine

The title compound was prepared according to procedures analogous to those described in Example 1. HPLC $t_R$=4.17 min, LC-MS=280 (M+1).

EXAMPLE 9

1-Methyl-6-[1-methyl-3-(6-methyl-pyridin-2-yl)-1H-pyrazol-4-yl]-1H-benzotriazole The title compound was prepared according to procedures analogous to those described in Example 1. HPLC $t_R$=3.79 min, LC-MS=305 (M+1).

EXAMPLE 10

4-(1-Methyl-3-pyridin-2-yl-1H-pyrazol-4-yl)-quinoline

The title compound was prepared according to procedures analogous to those described in Example 1. HPLC $t_R$=3.73 min, LC-MS=287 (M+1).

EXAMPLE 11

4-(1-Methyl-5-pyridin-2-yl-1H-pyrazol-4-yl)-quinoline

The title compound was prepared according to procedures analogous to those described in Example 1. HPLC $t_R$=3.9 min, LC-MS=287 (M+1).

EXAMPLE 12

6-[3-(6-Methyl-pyridin-2-yl)-1H-pyrazol-4-yl]-2-trifluoromethyl-[1,2,4]triazolo[1,5-a]pyridine The title compound was prepared according to procedures analogous to those described in Example 1. HPLC $t_R$=4.77 min, LC-MS=345 (M+1).

EXAMPLE 13

2-Isopropyl-6-[3-(6-methyl-pyridin-2-yl)-1H-pyrazol-4-yl]-[1,2,4]triazolo[1,5-a]pyridine The title compound was prepared according to procedures analogous to those described in Example 1. HPLC $t_R$=4.08 min, LC-MS=319 (M+1).

EXAMPLE 14

3-Methyl-6-[3-(6-methyl-pyridin-2-yl)-1H-pyrazol-4-yl]-[1,2,4]triazolo[4,3-a]pyridine The title compound was prepared according to procedures analogous to those described in Example 1. HPLC $t_R$=2.77 min, LC-MS=291 (M+1).

EXAMPLE 15

2-Methyl-6-[3-(6-methyl-pyridin-2-yl)-1H-pyrazol-4-yl]-[1,2,4]triazolo[1,5-a]pyridine The title compound was prepared according to procedures analogous to those described in Example 1. HPLC $t_R$=3.38 min, LC-MS=291 (M+1).

EXAMPLE 16

2-Methyl-5-[3-(6-methyl-pyridin-2-yl)-1H-pyrazol-4-yl]-2H-benzotriazole

The title compound was prepared according to procedures analogous to those described in Example 1. HPLC $t_R$=3.72 min, LC-MS=291 (M+1).

EXAMPLE 17

Preparation of 4-Methoxy-6-[3-(6-methyl-pyridin-2-yl)-1H-pyrazol-4-yl]-quinoline Step A: Preparation of 2-(4-Methoxy-quinoline-6-yl)-1-(6-methyl-pyridin-2-yl)-ethanone To a 20 mL threaded pressure tube was added 6-Chloro-4-methoxy-quinoline (298 mg, 1.54 mmol), palladium (II) acetate (7 mg, 0.03 mmol), 2-Dicyclohexylphosphino-2'-(N,N-dimethylamino)biphenyl (a.k.a. AMPHOS, 24 mg, 0.06 mmol), and potassium tert-butoxide (1 M in THF, 3.7 mmol). This mixture was stirred and 1-(6-Methyl-pyridin-2-yl)-ethanone was added. The pressure tube was then sealed and heated to 70° C. The reaction mixture was stirred at 70° C. for 18 hours. LC-MS showed product. The reaction mixture was then cooled and poured into a solution of 600 µL of glacial acetic acid in 30 mL of water. Title compound was extracted with 3×30 mL of chloroform. The organic layers were combined, dried over sodium sulfate, filtered, and concentrated via rotary evaporator. The residue was purified by flash column chromatography (silica gel) using a 1% Methanol/Chloroform solvent system affording 255 mg of desired product (56% yield). HPLC=4.39 min, LC-MS=293 (M+H, mw=292.34).

Step B: Preparation of 4-Methoxy-6-[3-(6-Methyl-Pyridin-2-yl)-1H-Pyrazol-4-yl]-Quinoline To a 10 mL flask was added 2-(4-Methoxy-quinolin-6-yl)-1-(6-methyl-pyridin-2-yl)-ethanone (70 mg, 0.17 mmol), and N,N-dimethylformamide dimethyl acetal (1.4 mL, 10.9 mmol). This solution was stirred at 80° C. for 2.5 hours, followed by concentration to complete dryness via rotary evaporator. The residue was dissolved in ethanol (1.5 mL) and hydrazine hydrate was added (63 mL, 1.02 mmol). This new reaction mixture was stirred at room temperature for 2.5 hours. LC-MS showed product. The reaction mixture was concentrated to dryness. The residue was purified by Shimodzu prep. HPLC using a 0-40% Acetonitrile/water solvent gradient (0.1% formic acid in both solvents) affording 28 mg of title compound (51% yield). HPLC=3.34 min, LC-MS=317 (M+H, mw=316.37).

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. Accordingly, the invention is limited only by the following claims.

What is claimed is:

1. A compound of formula (Ia):

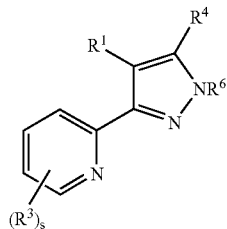

(Ia)

or a pharmaceutically acceptable salt thereof, wherein
$R^1$ is a pyridyl group;
$R^3$ is independently selected from the group consisting of: halo, halo($C_1$-$C_6$)alkyl, ($C_1$-$C_6$)alkyl, ($C_2$-$C_6$)alkenyl, ($C_2$-$C_6$)alkynyl, perhalo($C_1$-$C_6$)alkyl, phenyl, ($C_3$-$C_{10}$)cycloalkyl, hydroxy, ($C_1$-$C_6$)alkoxy, perhalo($C_1$-$C_6$)alkoxy, phenoxy, ($C_3$-$C_{10}$)cycloalkyl-O—, ($C_1$-$C_6$)alkyl-S—, ($C_1$-$C_6$)alkyl-SO$_2$—, ($C_1$-$C_6$)alkyl-NH—SO$_2$—, O$_2$N—, NC—, amino, Ph(CH$_2$)$_{1-6}$HN—, —($C_1$-$C_6$)alkyl HN—, ($C_1$-$C_6$)alkylamino, [($C_1$-$C_6$)alkyl]$_2$-amino, ($C_1$-$C_6$)alkyl-SO$_2$—NH—, amino(C=O)—, aminoO$_2$S—, ($C_1$-$C_6$)alkyl-(C=O)—NH—, ($C_1$-$C_6$)alkyl-(C=O)—[((($C_1$-$C_6$)alkyl)-N]—, phenyl-(C=O)—NH—, phenyl-(C=O)—[((($C_1$-$C_6$)alkyl)-N]—, —($C_1$$C_6$)alkyl-(C=O)—, ($C_3$-$C_{10}$)cycloalkyl-(C=O)—, HO—(C=O)—, ($C_1$-$C_6$)alkyl-O—(C=O)—, H$_2$N(C=O)—, ($C_1$-$C_6$)alkyl-NH—(C=O)—, [($C_1$-$C_6$)alkyl]$_2$-N—(C=O)—, phenyl-NH—(C=O)—, phenyl-[(($C_1$-$C_6$)alkyl)-N]—(C=O)—, ($C_3$-$C_6$)cycloalkyl-NH—(C=O)— and ($C_1$-$C_6$)alkyl-(C=O)—O—;
each of which is optionally substituted by at least one substituent independently selected from ($C_1$-$C_6$)alkyl, ($C_1$-$C_6$)alkoxy, halo($C_1$-$C_6$)alkyl, halo, H$_2$N—, Ph(CH$_2$)$_{1-6}$HN—, and ($C_1$-$C_6$)alkylHN—;
s is one;
$R^4$ is selected from the group consisting of: hydrogen, halo, halo($C_1$-$C_6$)alkyl, ($C_1$-$C_6$)alkyl, ($C_2$-$C_6$)alkenyl, ($C_2$-$C_6$)alkynyl, perhalo($C_1$-$C_6$)alkyl, phenyl, ($C_3$-$C_{10}$)cycloalkyl, hydroxy, ($C_1$-$C_6$)alkoxy, perhalo($C_1$-$C_6$)alkoxy, phenoxy, ($C_3$-$C_{10}$)cycloalkyl-O—, ($C_1$-$C_6$)alkyl-S—, ($C_1$-$C_6$)alkyl-SO$_2$—, ($C_1$-$C_6$)alkyl-NH—SO$_2$—, O$_2$N—, NC—, amino, Ph(CH$_2$)$_{1-6}$NH—, alkylNH—, ($C_1$-$C_6$)alkylamino, [($C_1$-$C_6$)alkyl]$_2$-amino, ($C_1$-$C_6$)alkyl-SO$_2$—NH—, amino(C=O)—, aminoSO$_2$—, ($C_1$-$C_6$)alkyl-(C=O)—NH—, ($C_1$-$C_6$)alkyl-(C=O)—(($C_1$-$C_6$)alkyl)-N]—, phenyl-(C=O)—NH—, phenyl-(C=O)—(($C_1$-$C_6$)alkyl)-N]—, ($C_1$-$C_6$)alkyl-(C=O)—, phenyl-(C=O)—, cycloalkyl-(C=O)—, HO—(C=O)—, ($C_1$-$C_6$)alkyl-O—(C=O)—, H$_2$N(C=O)—, ($C_1$-$C_6$)alkyl-NH—(C=O)—, (($C_1$-$C_6$)alkyl)$_2$-N—(C=O)—, phenyl-NH—(C=O)—, phenyl-(($C_1$-$C_6$)alkyl)-N]—(C=O)—, ($C_3$-$C_{10}$)cycloalkyl-NH—(C=O)— and ($C_1$-$C_6$)alkyl-(C=O)—O—;
each of which is optionally substituted by at least one substituent independently selected from the group consisting of ($C_1$-$C_6$)alkyl, ($C_1$-$C_6$)alkoxy, halo($C_1$-$C_6$)alkyl, halo, H$_2$N—, Ph(CH$_2$)$_{1-6}$—NH—, and ($C_1$-$C_6$)alkylNH—; and
$R^6$ is selected from the group of ($C_2$-$C_6$)alkenyl, ($C_2$-$C_6$)alkynyl, phenyl, ($C_3$-$C_{10}$)cycloalkyl, ($C_1$-$C_6$)alkyl-(SO$_2$)—, phenyl-(SO$_2$)—, H$_2$N—(SO$_2$)—, ($C_1$-$C_6$)alkyl-NH—(SO$_2$)—, (($C_1$-$C_6$)alkyl)$_2$N—(SO$_2$)—, phenyl-NH—(SO$_2$)—, (phenyl)$_2$N—(SO$_2$)—, ($C_1$-$C_6$)alkyl-(C=O)—, phenyl-(C=O)—, ($C_3$-$C_{10}$)cycloalkyl—(C=O)—, ($C_1$-$C_6$)alkyl-O—(C=O)—, ($C_3$-$C_{10}$)cycloalkyl-O—(C=O)—, H$_2$N—(C=O)—, ($C_1$-$C_6$)alkyl-NH—(C=O)—, phenyl-NH—(C=O)—, ($C_3$-$C_{10}$)cycloalkyl-NH—(C=O)—, (($C_1$-$C_6$)alkyl)$_2$N—(C=O)—, (phenyl)$_2$N—(C=O)—, phenyl-[(($C_1$-$C_6$)alkyl)-N]—(C=O)—, and ($C_3$-$C_{10}$)cycloalkyl-[(($C_1$-$C_6$)alkyl)-N]-(C=O)—;
each of which is optionally substituted with at least one moiety independently selected from the group consisting of halo, ($C_1$-$C_6$)alkyl, ($C_2$-$C_6$)alkenyl, ($C_2$-$C_6$)alkynyl, perhalo($C_1$-$C_6$)alkyl, ($C_3$-$C_{10}$)cycloalkyl, phenyl, benzyl, ($C_1$-$C_6$)alkyl-SO$_2$—, formyl, NC—, ($C_1$-$C_6$)alkyl-(C=O)—, ($C_3$-$C_{10}$)cycloalkyl-(C=O)—, phenyl-(C=O)—, HO—(C=O)—, ($C_1$-$C_6$)alkyl-O—(C=O)—, ($C_3$-$C_{10}$)cycloalkyl-O—(C=O)—, ($C_1$-$C_6$)alkyl-NH—(C=O)—, ($C_3$-$C_{10}$)cycloalkyl-NH—(C=O)—, phenyl-NH—(C=O)—, (($C_1$-$C_6$)alkyl)$_2$-N—(C=O)—, phenyl-[(($C_1$-$C_6$)alkyl)-N]—(C=O)—, hydroxy, ($C_1$-$C_6$)alkoxy, perhalo($C_1$-$C_6$)alkoxy, ($C_3$-$C_{10}$)cycloalkyl-O—, phenoxy, ($C_1$-$C_6$)alkyl-(C=O)—O—, ($C_3$-$C_{10}$)cycloalkyl-(C=O)—O—, phenyl-(C=O)—O—, O$_2$N—, amino, ($C_1$-$C_6$)alkylamino, (($C_1$-$C_6$)alkyl)$_2$-amino, formamidyl, ($C_1$-$C_6$)alkyl-(C=O)—NH—, ($C_3$-$C_{10}$)cycloalkyl-(C=O)—NH—, phenyl-(C=O)—NH—, ($C_1$-$C_6$)alkyl-(C=O)—[(($C_1$-$C_6$)alkyl)-N]—, phenyl-(C=O)—[($C_1$-$C_6$)alkyl-N]—, ($C_1$-$C_6$)alkyl-SO$_2$NH—, ($C_3$-$C_{10}$)cycloalkyl-SO$_2$NH—, and phenyl-SO$_2$NH—;
wherein the phenyl moiety of a $R^6$ substituent is optionally further substituted with at least one radical independently selected from the group consisting of halo, ($C_1$-$C_6$)alkyl, ($C_1$-$C_6$)alkoxy, perfluoro($C_1$-$C_6$)alkyl and perfluoro($C_1$-$C_6$)alkoxy.

2. A compound of claim 1, wherein $R^1$ is

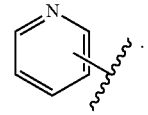

3. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,638,537 B2 | Page 1 of 1 |
| APPLICATION NO. | : 11/557638 | |
| DATED | : December 29, 2009 | |
| INVENTOR(S) | : Munchhof et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 51 days.

Signed and Sealed this

Sixteenth Day of November, 2010

David J. Kappos
*Director of the United States Patent and Trademark Office*